(12) United States Patent
Dailey et al.

(10) Patent No.: US 8,058,039 B2
(45) Date of Patent: Nov. 15, 2011

(54) USE OF ERYTHROMYCIN AS A SELECTIVE ANTIMICROBIAL AGENT IN THE PRODUCTION OF ALCOHOLS

(75) Inventors: Kevin E. Dailey, Suwanee, GA (US); Kevin L. Kauers, Duluth, GA (US)

(73) Assignee: North American Bioproducts Corporation, Duluth, GA (US)

( * ) Notice: Subject to any disclaimer, the term of this patent is extended or adjusted under 35 U.S.C. 154(b) by 359 days.

(21) Appl. No.: 12/076,032

(22) Filed: Mar. 13, 2008

(65) Prior Publication Data

US 2009/0233340 A1    Sep. 17, 2009

(51) Int. Cl.
    *C12P 7/06* (2006.01)
(52) U.S. Cl. ............ 435/161; 435/244; 514/29; 536/7.2
(58) Field of Classification Search .................. None
    See application file for complete search history.

(56) References Cited

U.S. PATENT DOCUMENTS

| | | |
|---|---|---|
| 4,568,644 A | 2/1986 | Wang et al. |
| 4,985,355 A | 1/1991 | Millichip |
| 5,554,520 A | 9/1996 | Fowler et al. |
| 2004/0044087 A1 | 3/2004 | Maye |
| 2004/0072312 A1 | 4/2004 | Yukawa |
| 2004/0234649 A1 | 11/2004 | Lewis et al. |
| 2005/0019924 A1 | 1/2005 | Hitzeman et al. |
| 2005/0233030 A1 | 10/2005 | Lewis et al. |
| 2005/0260554 A1 | 11/2005 | Gaalswyk |
| 2007/0031953 A1 | 2/2007 | Dunson, Jr. et al. |
| 2007/0281344 A1 | 12/2007 | Lantero et al. |
| 2007/0292919 A1 | 12/2007 | Holt et al. |

OTHER PUBLICATIONS

Basaraba et al., J Vet Diagn Invest, 1999, vol. 11, p. 79-86.*
Skinner et al., J Ind Microbiol. Biotechnol, 2004, vol. 31, p. 401-408.*
Danielsen et al., International Journal of Food Microbiology, 2003, vol. 82, p. 1-11.*
Swenson et al., Antimicrobial Agents and Chemotherapy, 1990, vol. 34, No. 4, p. 543-549.*
Bisakowski, B., et al., "Effect of Lactic Acid Fermentation of Onions (*Allium cepa*) on the Composition of Flavonol Glucosides", Intern. J Food Sci Technol, 2007, 42: 783-789.
Florez, A.B., et al., "Antimicrobial Susceptibility of Lactic Acid Bacteria Isolated from a Cheese Environment", Can. J. Microbiol, 2005, 51: 51-58.
Narendranath, N.V., "Chapter 20 Bacterial contamination and control in ethanol production", The Alcohol Text Book, 4th Edition, 2003, p. 287-298, Nottingham University Press.

* cited by examiner

*Primary Examiner* — Kade Ariani
(74) *Attorney, Agent, or Firm* — Welsh Flaxman & Gitler LLC

(57) ABSTRACT

A process for the use of low concentration levels of Erythromycin to eliminate or control the growth of unwanted or undesirable bacteria (contaminating bacteria) in the fermentation production of alcohols without inhibition of the growth or replication of the yeast.

6 Claims, 1 Drawing Sheet

USE OF ERYTHROMYCIN AS A SELECTIVE ANTIMICROBIAL AGENT IN THE PRODUCTION OF ALCOHOLS

FIELD OF THE INVENTION

The present invention relates to the use of a selective antimicrobial in the production of fuel alcohols, beverage alcohols and industrial alcohols by fermentation to control the growth of non-preferred, contaminating microorganisms during the yeast propagation phase and fermentation phase of production, wherein the selective antimicrobial is Erythromycin.

BACKGROUND OF THE INVENTION

The recent expansion of the bio-fuels industry has fueled the popularity of ethanol and the effects of ethanol on the environment, economy and US national policy. Antibiotics have been used in fermentations during the production of fuel alcohol since its inception dating back to the 1970's. The co-products (distiller's grains) resulting from these fermentations have been fed to livestock increasingly over the past 3 decades with a particularly sharp increase of 340% from 1999 to 2005 to 8.35 million metric tons of distiller's grains in the United States alone. Most (98%) of the distiller's grains in North America come from plants that produce ethanol for oxygenated fuels.

Alcohol is produced by yeast fermentation, primarily of carbohydrates derived from starch-based or sugar-based feedstocks. This fermentation is provided by yeast, specifically the microorganism *Saccharomyces cerevisea* that ferments the available carbohydrates to produce ethanol. The entire process of alcohol production is well documented in "The Alcohol Text Book", $4^{th}$ edition, Jacques, Lyons & Kelsall, published by Nottingham University Press, 2003, which is incorporated herein by reference.

One of the important concerns with a conventional fermentation system is the difficulty of maintaining a sterile condition free from contaminating bacteria in the large-sized batches during the long fermentation period. Unfortunately, the optimum atmosphere for fermentation is also extremely conducive to bacterial growth. Should a batch become contaminated, not only must the fermentation mixture (i.e. the yeast, feedstock, nutrients, water, etc.) be discarded, but the entire fermentation vessel must be emptied, cleaned and sterilized, adding unwanted costs and loss of production.

It is common in current commercial fermentation processes that contaminating bacteria will infect the fermentations and consume the available carbohydrate to produce organic acids consequently causing less carbohydrate availability to the preferred yeast fermentation. Contamination by bacteria is very costly to the ethanol producer and a variety of control methods are utilized to limit this event. It is commonplace in most ethanol producing facilities to utilize caustic washing via clean in place systems.

The origin of these contaminants is multi-faceted and is being researched by researchers and producers alike. However, it is generally accepted that much of the bacteria originates from the incoming feedstock since the starch crops are often contaminated with bacteria from the field and storage silos. Jet cooking the fermentation substrate (mash) helps lower the bacteria count, but does not completely eliminate the contaminants as this process is not a sterilization procedure and bacteria contamination is unavoidable as these production facilities are not sterile production environments like those commonly found in the pharmaceutical industry.

The increased popularity of the bio-fuels industry, along with the increased supply of distiller's co-products, has caused heightened awareness and concerns regarding antimicrobials being used during the fermentation process as the antimicrobials may "carry through" to the resulting distiller's co-products.

The industry is currently awaiting more direct guidance from the FDA (Food & Drug Administration) and the CVM (Center for Veterinary Medicine) as well as certain state agencies (where applicable) on the allowable use of antimicrobials as a processing aid in ethanol production Therefore, an economical method to selectively control contaminating bacteria is needed. The method must utilize smaller amounts of an antibiotic then currently being used to target and act bactericidal and/or bacteristatic to control contaminating bacteria in a fermentation, such as a bacterial contaminant found in the production of fuel alcohols, beverage alcohols and industrial alcohols while improving production yield. Additionally, distiller's co-products of the fermentation must be safe for direct feeding to animals, i.e., the antibiotic used must not be detectable in the distiller's co-products so as to comply with increasing state and federal regulation. From the alcohol producer's point of view, the antibiotic needs to be cost effective and would be of more value if it did not have a deleterious effect on the yeast, thus producing more alcohol. Further, the antibiotic needs to be less susceptible to resistance by the targeted bacteria and be effective in low concentrations while not carrying through to the distiller's grains.

SUMMARY OF THE INVENTION

Figure 1:
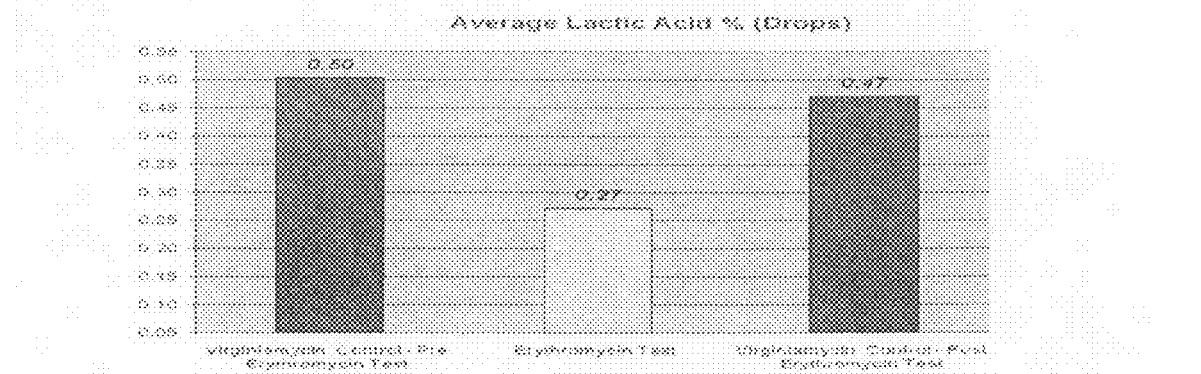
FIG. 1 is a graphical representation of the data from table 2.

The methods provided herein employ Erythromycin compositions to reduce or inhibit the growth of undesired bacteria. For example, the compositions may be used in an industrial fermentation system to reduce the growth of competing bacteria and enhance efficiency and/or yield during the industrial fermentation of fuel, beverage and industrial alcohols as a new and unique method of use for Erythromycin.

It is, therefore, an object of the present invention to provide a method for increasing the amount of alcohol produced during large scale alcohol production. The method is achieved by introducing an antibiotic as an active agent to a vessel used during alcohol production to render an ideal environment for a fermentation mixture when combined with the antibiotic for fermenting the fermentation mixture into the desired alcohol. The active agent functions to substantially reduce any deleterious effects of at least one contaminating bacteria present in the fermentation mixture while not having any deleterious effects on the yeast. The active agent is added to the vessel in an amount ranging from at least 0.5 ppm to about 6 ppm of the fermentation mixture and is selected from the group consisting of Erythromycin and derivatives or salts of Erythromycin.

It is also an object of the present invention to provide a method wherein the antibiotic is added in an amount ranging from 0.5 to 3 ppm of the fermentation mixture.

It is another object of the present invention to provide a method wherein the alcohol produced is ethanol.

It is a further object of the present invention to provide a method wherein the vessel is a fermentation tank and the antibiotic is introduced therein.

It is still another object of the present invention to provide a method wherein the vessel is a yeast propagation tank and the antibiotic is introduced therein.

It is yet another object of the present invention to provide a method wherein the fermentation mixture is derived from any feedstock selected from the group consisting of: corn, wheat, triticale, barley, cassava, rye, graded starch stream rendered from the feedstocks, sugar cane, sugar beet, molasses, rice straw, potato waste, wood waste, switch grass, pine and other wood derivatives, municipal waste, food waste, alcoholic and non-alcoholic beverage industry waste and mixtures thereof.

It is also an object of the present invention to provide a method wherein in addition to alcohol being produced co-products result and the antibiotic in these co-products is low or at non-detectable level.

It is a further object of the present invention to provide a method wherein the antibiotic is present in a low or non-detectable level in the produced co-products.

It is still a further object of the present invention to provide a method wherein the antibiotic functions to inhibit protein synthesis at a ribosomal level thus controlling or lysing the contaminating bacteria growth while being unable to penetrate the nucleus of the yeast cell thus rendering the antibiotic harmless to yeast during fermentation.

It is yet a further object of the present invention to provide a fermentation mixture used in the production of ethanol comprising yeast, carbohydrates and 0.5 ppm to about 6 ppm of Erythromycin and derivatives or salts of Erythromycin, wherein the Erythromycin inhibits growth of microorganisms competing for the yeast thereby increasing the amount of alcohol produced from the fermentation mixture.

It is also an object of the present invention to provide a method for controlling the growth of lactic acid bacteria in a fermentation process for the production of alcohol. The method includes the steps of adding a minimum inhibitory concentration of Erythromycin and derivatives or salts of Erythromycin to a vessel and the Erythromycin becoming part of a fermentation mixture used in making alcohol, wherein the vessel is susceptible to lactic acid bacteria, and wherein the addition of the minimum inhibitory concentration of Erythromycin to the vessel controls the growth of lactic acid bacteria.

These and other objects, features and advantages of the present invention will become apparent after a review of the following detailed description of the disclosed embodiments and claims.

DETAILED DESCRIPTION OF THE INVENTION

As previously stated, the production of commercial alcohol, specifically the production of fuel grade alcohol, predominantly ethanol, has increased in popularity and past and current legislation has led to a trend of investment into manufacturing capacity and developing production efficiencies.

Over the past decades Erythromycin has gained popularity as a commonly used antimicrobial for use in animal and human clinical health as referenced in U.S. Pat. Nos. 6,100, 404 and 6,440,941. Unlike any previously disclosed applications of the use of Erythromycin, the present invention illustrates that Erythromycin is efficacious for use in the commercial production of alcohol. Furthermore, the present invention relates to a method of use for Erythromycin having a significantly different set of criteria for efficaciousness than that involved with human clinical health.

As employed in accordance with a preferred embodiment of the present invention, Erythromycin is effective against bacteria commonly found in the production of fuel alcohols, beverage alcohols and industrial alcohols, and is more effective than other commonly used antibiotics against industry-specific isolated bacteria. The alcohols produced for fuel, beverage and industrial use are oftentimes manufactured in the same facility utilizing the same fermentation technique. The use and effectiveness of Erythromycin are realized to the same degree in the same fermentation process producing ethanol for all the three categories, namely fuel, beverage and industrial applications.

Briefly, the present invention provides a method for increasing the amount of alcohol produced during large scale alcohol production. The method is achieved by introducing an antibiotic as an active agent to a vessel used during alcohol production to render an ideal environment for a fermentation mixture when combined with the antibiotic for fermenting the fermentation mixture into the desired alcohol. The active agent functions to substantially reduce any deleterious effects of at least one contaminating bacteria present in the fermentation mixture while not having any deleterious effects on the yeast. The active agent is added to the vessel in an amount ranging from at least 0.5 ppm to about 6 ppm of the fermentation mixture and is selected from the group consisting of Erythromycin, Erythromycin Phosphate, Erythromycin Thiocyanate and derivatives or salts of Erythromycin.

In addition, Erythromycin, when used in accordance with the present invention, has the propensity to render a low (or no) detection level in distiller's co-products when added during the alcohol production process in amounts/concentrations disclosed in the present application. Erythromycin used in accordance with the present invention is not deleterious to the preferred fermentation organism; yeast (*Saccharomyces cerevisea*) in the low oxygen environment associated with the production of alcohol. In addition, Erythromycin has a very specific mode of action when used during fermentation. Although a macrolide, its mode of action is very specific and makes it unlike any other antimicrobial commonly used in the production of alcohol.

Erythromycin Operation

The Erythromycin added during the alcohol production process in accordance with the present invention is a very effective antibiotic against lactic acid bacteria such as *Lactobacillus* species. The prevention of the growth of lactic acid bacteria during alcohol production is beneficial.

Erythromycin works by inhibiting protein synthesis in susceptible bacteria by interfering with the ability of ribosomes to translate messenger RNA (mRNA) into proteins vital to life processes. Proteins are important to life processes and are required for the breakdown of growth substrates, such as carbohydrates, and help regulate the flow of metabolites in and out of the cell. The process whereby proteins are manufactured is referred to as protein synthesis. In order for proteins to be made, the "blueprint" or "instructions" for making a particular protein is retrieved from the DNA that lies within the chromosome. The pieces of DNA that serve as the "instruction manual" for building a protein are called genes. Genes are copied from DNA into messenger RNA (mRNA) during a process called transcription. The mRNA then serves as the "message" telling the ribosomes, located throughout the cytoplasm (the area inside the cell), how to assemble or build proteins using various amino acids as building blocks (translation). Certain, antibiotics that affect protein synthesis, like Erythromycin, are considered "macrolide antibiotics" and affecting the ribosome's ability to translate the mRNA into proteins.

Even though there are other antibiotics that can inhibit protein synthesis, the macrolide Erythromycin has a very specific mechanism as it binds to the mRNA at a very unique and specific point and inhibits the activity of the ribosome. This specific method of inhibiting protein synthesis as applied in accordance with the present invention has been determined to be unique to Erythromycin and not like any other macrolide antibiotic commonly used in alcohol production.

The primary bacteria of concern in alcohol production processes are gram positive bacteria of, but not limited to, the *Lactobacillus* and *Pediococcus* species. Erythromycin utilized in alcohol production in accordance with the present invention efficaciously controls gram positive bacteria specifically present in the production of fuel alcohol, beverage alcohol and industrial alcohol.

Erythromycin works by inhibiting protein synthesis at a ribosomal level. Ribosomes in gram positive bacteria float freely in the cytoplasm of the cell whereas the ribosomes in yeast are situated along its endoplasmic reticulum, an extension of the nuclear membrane of the cell. It is believed that Erythromycin cannot penetrate the nuclear membrane of the yeast cell which along with the in ability to bind to the ribosomes, appears to render the antimicrobial harmless to yeast during fermentation while controlling contaminating gram positive bacterial growth.

Upon the consumption of sugar during fermentation, gram positive bacteria produce organic acids. These contaminating bacteria are able to convert one mole of glucose into two moles of lactic acid. Therefore, for every gram of lactic acid formed, nearly two grams of glucose is lost which represents a one-gram loss in alcohol produced by the preferred organism (that is, yeast). This occurrence is very costly to the producer where a 1% lactic acid production level represents an approximate loss of 1% of alcohol by weight. The detrimental effect of lactic acid is a well documented fact as it occurs in many fermentation processes. Numerous researchers have worked toward managing this yeast stress factor as documented in one of the journals by Dr. Scott Kohl in Ethanol Today, January 2004, "Ethanol 101-5: Managing stress factors. The economics and efficiency of fermentation processes are frequently such that ethanol producers cannot tolerate any such loss of production. If no antibiotics are used, a 1 to 5 percent loss in ethanol yield is common. A fifty million-gallon (annual capacity) fuel ethanol plant operating with a lactic acid level of 0.3 percent weight/weight in its distiller's beer is losing roughly 570,000 gallons of ethanol every year due to bacteria.

Erythromycin when used in accordance with the present invention in the production of alcohol exhibits a high degree of effectiveness when controlling the growth and/or lysing of contaminant bacteria. The present invention offers several advantages to using Erythromycin over the use of other antibiotics in the commercial alcohol production process. Low concentration levels of Erythromycin, in accordance with the present invention, were found to control the growth of bacteria that are tolerant or resistant to other antibiotics. In fact, lower concentration levels of Erythromycin are needed over a shorter period of time to achieve the same amount of bacterial control compared with other antibiotics known in the art. Therefore, Erythromycin is capable of eliminating certain contaminating bacteria more rapidly and effectively than other commonly used antibiotics. Also, and due to the small concentration levels of Erythromycin used in accordance with the present invention, the Erythromycin does not carry through to the co-products produced. That is, there is no detectable antimicrobial in the distillers co-products rendered from fermentations employing Erythromycin used in accordance with the present invention.

Since antibiotics are costly, lower levels used during the alcohol production process relates directly to a reduction in the cost per liter of alcohol when produced in accordance with the present method.

The present invention provides methods and compositions for enriching the fermentation mixture to optimize and foster the growth and replication of *Saccharomyces cervisea* yeast while reducing or preventing growth or replication of undesirable bacteria.

Erythromycin Compositions

Erythromycin is an antibiotic substance produced by a strain of *Streptomyces erythreus* found in a soil sample from the Philippine Archipelago (Erythromycin is the subject of U.S. Pat. Nos. 2,653,899 and 2,823,203 which are incorporated herein by reference). For purposes of this invention, the term Erythromycin pertains to the compound Erythromycin and any close derivatives or salts thereof, such as Erythromycin Phosphate or Erythromycin in its unrefined form Erythromycin Thiocyanate. Erythromycin Thiocyanate is a source product of Erythromycin that is a feed grade product refined to remove its sulfur component to render a human grade product that is more water soluble. Acid addition salts of Erythromycin which may be utilized are the salts formed with acetic, propionic, trifluoroacetic, maleic, tartaric, methanesulphonic, benzenesulphonic, p-toluenesulphonic acid and the like, and especially stearic, ethylsuccinic or laurysulphonic acid Erythromycin-based antibiotics, in particular Bactenix V200 available from North American Bioproducts Corporation (NABC), referred to in the present invention as Erythromycin, Bactenix V200 or V200 has a composition that is stabilized in a dry form and is preferably added in the alcohol production process to a vessel during the propagation and fermentation steps to combine with the fermentation mixture prior to, during or after the introduction of *Saccharomyces* yeast to the process. Although, it is contemplated that the Erythromycin can be added to anyone of the vessels or tanks used during the production of alcohol, such as the mix tank, liquification tank, saccharification tank, propagation tank and/or fermentor.

Erythromycin as the selective agent functions to reduce, eliminate or control the growth of unwanted or undesirable bacteria in a fermentation mixture without inhibiting the growth or replication of a microorganism of interest (yeast), and the methods described herein utilize the composition to enrich the fermentation mixture to foster optimal growth of the desirable microorganism during the propagation and fermentation phase of commercial alcohol production. Erythromycin may be used as a single ingredient finished product antibiotic or as a component of a combinatory finished product, or in conjunction with any other antimicrobial known as useful in this process by those skilled in the art in this process.

Method of Increased Alcohol Production

Large scale alcohol fermentation is often done in a two-step process. First one propagates the yeast in a propagation tank forming an inoculum. Then this inoculum is transferred to a much larger fermentation tank (fermentor) and mixed with a previously created fermentation mixture/mash. Generally, the fermentation mixture is created by added water and fermentation substrates/feedstock together in a mixing tank, then transferring this mixture to a liquification tank where alpha-amylase is added and then transferring this mixture to a saccharification tank where additional enzymes are added. The resulting fermentation mixture generally contains, feedstock (carbohydrates), nutrients, water, etc. and often referred to as mash. The mash usually containing between 30-35% solids. The nutrients help the yeast cells grow to be extremely strong and healthy. Therefore, the yeast performs better in the fermentor, giving a better fermentation that complete to dryness.

As briefly discussed above the present invention provides a method for increasing the amount of alcohol produced during large scale alcohol production. The method involves introducing an antibiotic as an active agent, preferably, to a fermentation mixture in a vessel during alcohol production to render an ideal environment for fermentation of the fermentation mixture into a desired alcohol with yeast capable of fermenting the fermentation mixture into the desired alcohol under conditions suitable to promote fermentation. Although in accordance with a preferred embodiment, the antibiotic is added to the fermentation tank or the propagation tank, the antibiotic may be added to anyone of the tanks used during the alcohol production process as it will ultimately combine with the fermentation mixture. The active agent functions to substantially reduce any deleterious effects of at least one of the contaminating bacteria present in said fermentation mixture while not having any deleterious effects on the yeast.

Specifically, the active agent is added to the mixture in an amount ranging from at least 0.5 ppm to about 6 ppm of fermentation mixture and is selected from the group consisting of Erythromycin, Erythromycin Phosphate, Erythromycin Thiocyanate and derivatives or salts of Erythromycin.

In large scale industrial production of ethanol we have found Erythromycin works best if the fermentation temperature is maintained between approximately 30-38° C. and the pH is maintained between approximately 2.5 to 6, more specifically approximately 4.5 to 6. In industrial alcohol fermentation, the fermentation mixture to which the Erythromycin composition is added is an extremely large volume (10,000-1,000,000 gallons). In accordance with the present invention, the Erythromycin is preferably added during the propagation and fermentation phase of the alcohol production in an effective amount for controlling or lysing of undesirable bacteria in amounts of at least 0.2 ppm, preferably at least 0.5 ppm of Erythromycin per amount of fermentation mixture to be treated, preferably between 0.5 to about 6 ppm, and most preferably 0.5 to 3 ppm.

Bacterial cells contemplated for treatment by the present methods include, but are not limited to, bacterial cells found to be contaminating systems of commercial significance, such as those used in commercial fuel alcohols, beverage alcohols and industrial alcohols production regardless of feedstock. Such bacteria include, but are not limited to, organisms such as *Lactobacillus* spp., *Pediococcus* spp., *Brevibaacterium* spp., and *Acetobacter* spp. used during ethanol production.

Benefits of Using Erythromycin

The use of such small amounts of Erythromycin does not deleteriously effect the fermentation production of alcohols in any manner, does not produce any undesirable side effects to the yeast, does not carry through to the distillers co-products and results in an increase in the amount of alcohol produced.

The Erythromycin compositions and methods provided herein are suitable to reduce, inhibit, or eliminate undesirable or contaminating bacterial species and strains commonly found in the production of ethanol while increasing the amount of ethanol produced. Thus, while antimicrobial use during alcohol production is not a new concept, it has been determined herein that a small amount of Erythromycin is an extremely efficacious control agent for the specific bacteria that are commonly found in the alcohol production environment. Specifically, Erythromycin at these concentration levels is thought to not be able to penetrate the nuclear membrane of the yeast cell, which along with the inability to bind to the ribosome subunits, prevents the Erythromycin antimicrobial from harming the yeast. Not harming the yeast during fermentation is important as it allows the yeast to propagate and ferment while preventing the contaminating bacteria from consuming more carbohydrates, resulting in greater alcohol production. The binding site for this antibiotic is specific to bacterial ribosomes and while a similar site exists on the yeast ribosome, antibiotic binding does not occur. As an example, work recently published by Bommankanti et al in RNA (14: 460-464, 2008) entitled "Mutation from guanine to adenine in 25S rRNA at the position equivalent to *E. coli* A2058 does not confer erythromycin sensitivity in *Saccharomyces cerevisea*+ demonstrates the inability of erythromycin to bind to the yeast ribosome subunits."

The presence of undesirable bacteria in the fermentation can have the effect of reducing production rates of the desired alcohols, as well as promoting the production of undesirable by-products such as organic acids and glycerol. The use of Erythromycin results in enhanced production of the desired alcohol product produced by the yeast. The methods provided herein are particularly useful because the feedstock or starting material in the alcohol production process is not sterile and therefore typically contain contaminating microorganisms.

Examples of feedstocks include (but are not limited to) corn, wheat, triticale, barley, cassava, rye, graded starch stream rendered from the aforementioned feedstocks, sugar cane, sugar beet, molasses, rice straw, potato waste, wood waste, switch grass, pine and other wood derivatives, municipal waste, food waste and beverage (alcoholic and non-alcoholic) industry waste. With such materials serving as feedstock it is not surprising that most commercial fermentations take place in the presence of significant bacterial contamination. *Lactobacilli* are the major contaminants in ethanol production and their presence and resultant lactic acid production reduces ethanol yield and creates a variety of stress factors that adversely affect yeast growth.

In the chemical antimicrobial agent marketplace, it is difficult work to identify a new antimicrobial that will offer efficacious control of bacteria specific to the alcohol production process that is not cost prohibitive. In this sense, it is unusual that such a small amount of Erythromycin would be effective in controlling undesirable bacteria (specific to this process) in a propagation cycle of alcohol production for approximately 10 hours. Furthermore, it is unexpected that such a small concentration of Erythromycin would be effective in controlling undesirable bacteria (specific to this process) in a fermentor for alcohol production for approximately 50 hours. Thus, the process of the present invention provides the benefits of both: 1) little or no undesirable side effects; and 2) extended production time efficacy.

Comparative Study

The following examples depict the efficacy of Erythromycin in alcohol production in accordance with the present invention and are not intended to limit the present invention, but are provided to aid in the understanding of the usefulness of Erythromycin-based antibiotic, such as Bactenix V200, in selectively controlling bacteria even when added in miniscule amounts.

The antibiotics currently most often used at alcohol production plants are either Penicillin-based or Virginiamycin-based. This example compares the use of Bactenix V200, an Erythromycin-based antibiotic versus V100, a Virginiamycin-based antibiotic also available from NABC to control Pediococcus test organism along with "industry normal" Lactobacillus. The trial uses an alcohol water mixture to assure total dissolving of antibiotics. This assures that the correct concentrations of antibiotics are going into the test wells and thereby preventing under dosing during the trial. All bacteria tested were industry specific isolates that were obtained from actual mash samples from alcohol production plants. The trial was set up as follows:

1. Dissolve 0.1 g of each of the antibiotics in 1 ml water and then add 5 ml of ethanol, vortex and bring up to 10 ml with sterile water to from a suspension.
2. Dilute the previous suspension 1:10 with sterile water. This gives a one mg/ml concentration.
3. Filter the suspension by running through a 0.2 μm syringe filter.
4. Add antibiotics to MRS (DeMan, Rogosa and Sharpe) broth at the concentrations required for the test.
5. Take two μl of a fresh 24-hour culture of the target organisms and add to the corresponding empty wells in a pre-labeled 24 well tissue culture plate.
6. Add one ml of the appropriate antibiotic media to each well of the plate.
7. Incubate at 33° C. for 24 hours.
8. Read plates for bacterial growth and re-incubate the plates at 33° C.
9. After 48 hours read and report the final results.

As displayed in Table 1 below, Erythromycin was effective at 0.5 ppm against all organisms tested. Virginiamycin was not effective against all organisms tested and showed an inability to control an industry obtained Pediococcus bacteria up to a 3.0 ppm inclusion rate.

Fermentation kinetics was measured for three batch cycles including:

Set 1—"Pre Erythromycin trial"—28 fermentor batches using a level of 0.5 ppm Virginiamycin. See results in Table 2.

Set 2—"Erythromycin trial"—27 fermentor batches using a level of 0.5 ppm of Erythromycin. See results in Table 3.

Set 3—"Post Erythromycin trial"—8 fermentor batches using a level of 0.5 ppm of Virginiamycin. See results in Table 4.

TABLE 2

Virginiamycin control drop data - "Pre Erythromycin trial"

| Ferm # | Batch # | Lactic % | Acetic % | EtOH % | Glucose % |
|---|---|---|---|---|---|
| 1 | 5954 | 0.32 | 0.05 | 16.94 | 0.29 |
| 4 | 5955 | N/r | n/r | N/r | n/r |
| 5 | 5956 | N/r | n/r | N/r | n/r |
| 6 | 5957 | 0.36 | 0.02 | 15.96 | 0.26 |
| 7 | 5958 | 0.51 | 0.03 | 15.96 | 0.17 |
| 1 | 5959 | 0.39 | 0.02 | 15.76 | 0.26 |
| 4 | 5960 | 0.28 | 0.03 | 15.77 | 0.32 |
| 5 | 5961 | 0.27 | 0.02 | 16.01 | 0.26 |
| 6 | 5962 | 0.57 | 0.03 | 15.88 | 0.28 |
| 7 | 5963 | 0.584 | 0.04 | 15.31 | 0.31 |
| 1 | 5964 | N/r | n/r | N/r | n/r |
| 4 | 5965 | N/r | n/r | N/r | n/r |
| 5 | 5966 | 0.33 | 0.03 | 15.34 | 0.33 |
| 6 | 5967 | 0.59 | 0.04 | 15.46 | 0.16 |
| 7 | 5968 | 0.71 | 0.04 | 15 | 0.3 |
| 1 | 5969 | 0.41 | 0.03 | 15.39 | 0.26 |
| 4 | 5970 | 0.36 | 0.03 | 14.64 | 0.45 |

TABLE 1

Virginiamycin (V100) vs. Erythromycin (V200) comparative efficacy analysis

| | V100 | V200 | V100 | V200 | V100 | V200 | V100 | V200 | V100 | V200 |
|---|---|---|---|---|---|---|---|---|---|---|
| Concentration | 0.5 ppm | | 0.75 ppm | | 1 ppm | | 2 ppm | | 3 ppm | |
| L. brevis | - | | - | | - | | - | | - | |
| | - | | - | | - | | - | | - | |
| | - | | - | | - | | - | | - | |
| L. fermentum | 1 | | - | | - | | - | | - | |
| | 1 | | - | | - | | - | | - | |
| | 1 | | - | | - | | - | | - | |
| L. plantarum/pentosus | + | | - | | + | | - | | + | |
| | + | | + | | + | | - | | - | |
| | + | | + | | + | | + | | - | |
| Pediococcus | 1 | | 1 | | 1 | | 1 | | 1 | |
| | 1 | | 1 | | 1 | | 1 | | 1 | |
| | 1 | | 1 | | 1 | | 1 | | 1 | |

Note:
White squares are 24 hour readings, shaded squares are 48 hour readings, a negative (−) sign is indicative of no observed growth, a positive (+) sign is indicative of some observed growth and a one (1) sign is indicative of substantial observed growth.

An alcohol production plant trial was set up to confirm and replicate the positive results found in the laboratory that Erythromycin (V200) was more effective than Virginiamycin (V100) in controlling bacteria encountered in ethanol production. This trial was conducted at a 50 million gallon per year (m/g/y) dry grind fuel alcohol production facility utilizing corn as a fermentation substrate. Batch yeast propagation and fermentation process were utilized. Antimicrobials were added to the fermentor during the fill cycle at approximately 30% fill. No other changes were made to the process or chemical additions that would influence the fermentation kinetics monitored during 3 sets of fermentor batches listed below. The fermentation data was accumulated at the end (drop) of the fermentation process for each of the fermentors.

TABLE 2-continued

Virginiamycin control drop data - "Pre Erythromycin trial"

| Ferm # | Batch # | Lactic % | Acetic % | EtOH % | Glucose % |
|---|---|---|---|---|---|
| 5 | 5971 | N/r | n/r | N/r | n/r |
| 6 | 5972 | 0.59 | 0.02 | 15.66 | 0.36 |
| 7 | 5973 | 0.51 | 0.02 | 15.7 | 0.26 |
| 1 | 5974 | N/r | n/r | N/r | n/r |
| 4 | 5975 | 0.71 | 0.04 | 15.64 | 0.27 |
| 5 | 5976 | 0.71 | 0.04 | 15.5 | 0.26 |
| 6 | 5977 | 0.85 | 0.04 | 15.58 | 0.31 |
| 7 | 5978 | 0.62 | 0.04 | 15.93 | 0.29 |
| 1 | 5979 | 0.56 | 0.04 | 15.40 | 0.29 |

TABLE 2-continued

Virginiamycin control drop data - "Pre Erythromycin trial"

| Ferm # | Batch # | Lactic % | Acetic % | EtOH % | Glucose % |
|---|---|---|---|---|---|
| 4 | 5980 | 0.5 | 0.04 | 15.94 | 0.3 |
| 5 | 5981 | 0.52 | 0.04 | 15.83 | 0.31 |
| 6 | 5982 | 0.79 | 0.13 | 15.16 | 0.3 |
| 7 | 5983 | 0.68 | 0.04 | 15.82 | 0.3 |
| 1 | 5984 | 0.33 | 0.03 | 15.40 | 0.3 |
| 4 | 5985 | 0.32 | 0.04 | 15.94 | 0.31 |
| 5 | 5986 | 0.34 | 0.04 | 15.74 | 0.31 |
| 6 | 5987 | 0.39 | 0.04 | 16.05 | 0.31 |
| 28 | Batch average | 0.50 | 0.04 | 15.67 | 0.29 |

TABLE 3

Erythromycin test drop data - "Erythromycin trial"

| Ferm # | Batch # | Lactic % | Acetic % | EtOH % | Glucose % |
|---|---|---|---|---|---|
| 7 | 5988 | 0.38 | 0.03 | 15.98 | 0.35 |
| 1 | 5989 | 0.25 | 0.04 | 15.81 | 0.42 |
| 2 | 5990 | 0.22 | 0.04 | 16.21 | 0.32 |
| 5 | 5991 | 0.22 | 0.04 | 16.09 | 0.31 |
| 6 | 5992 | 0.27 | 0.06 | 15.67 | 0.53 |
| 7 | 5993 | 0.26 | 0.03 | 15.93 | 0.28 |
| 1 | 5994 | 0.26 | 0.03 | 15.91 | 0.28 |
| 2 | 5995 | 0.24 | 0.04 | 16.07 | 0.3 |
| 5 | 5996 | 0.24 | 0.04 | 15.51 | 0.28 |
| 6 | 5997 | 0.26 | 0.04 | 16.61 | 0.27 |
| 7 | 5998 | 0.28 | 0.03 | 15.95 | 0.28 |
| 1 | 5999 | 0.3 | 0.03 | 15.67 | 0.24 |
| 2 | 6000 | 0.27 | 0.03 | 15.58 | 0.28 |
| 5 | 6001 | 0.17 | 0.04 | 15.58 | 0.3 |
| 6 | 6002 | 0.19 | 0.05 | 15.96 | 0.3 |
| 7 | 6003 | 0.2 | 0.02 | 15.92 | 0.28 |
| 1 | 6004 | 0.25 | 0.03 | 15.75 | 0.27 |
| 2 | 6005 | 0.24 | 0.03 | 15.86 | 0.26 |
| 5 | 6006 | 0.24 | 0.03 | 15.81 | 0.26 |
| 6 | 6007 | 0.27 | 0.04 | 15.88 | 0.25 |
| 7 | 6008 | 0.37 | 0.05 | 15.39 | 0.25 |
| 1 | 6009 | n/r | n/r | N/r | n/r |
| 2 | 6010 | 0.31 | 0.04 | 15.74 | 0.28 |
| 5 | 6011 | 0.22 | 0.05 | 15.63 | 0.28 |
| 6 | 6012 | 0.32 | 0.04 | 15.59 | 0.26 |
| 7 | 6013 | 0.39 | 0.03 | 16.02 | 0.28 |
| 1 | 6014 | 0.38 | 0.04 | 15.69 | 0.31 |
| 2 | 6015 | 0.34 | 0.03 | 15.74 | 0.31 |
| 27 | Batch average | 0.27 | 0.04 | 15.84 | 0.30 |

TABLE 4

Virginiamycin control drop data - "Post Erythromycin test"

| Ferm # | Batch # | Lactic % | Acetic % | EtOH % | Glucose % |
|---|---|---|---|---|---|
| 5 | 6016 | 0.38 | 0.03 | 15.73 | 0.31 |
| 6 | 6017 | 0.43 | 0.05 | 15.78 | 0.33 |
| 7 | 6018 | 0.38 | 0.04 | 15.5 | 0.3 |
| 1 | 6019 | 0.50 | 0.04 | 15.56 | 0.32 |
| 2 | 6020 | 0.40 | 0.05 | 15.52 | 0.31 |
| 5 | 6021 | 0.44 | 0.04 | 15.77 | 0.35 |
| 6 | 6022 | 0.54 | 0.03 | 15.53 | 0.29 |
| 7 | 6023 | n/r | n/r | N/r | n/r |
| 1 | 6024 | 0.70 | 0.03 | 15.28 | 0.31 |
| 8 | Batch average | 0.47 | 0.04 | 15.58 | 0.32 |

The fermentors (Set 2) treated with Erythromycin utilized the same amount of glucose, had a decrease in lactic acid and an increase in final ethanol production when compared to the fermentors (Sets 1 and 3) treated with the same amount of Virginiamycin. See the graphs in FIGS. 1, 2 and 3.

Figure 2:
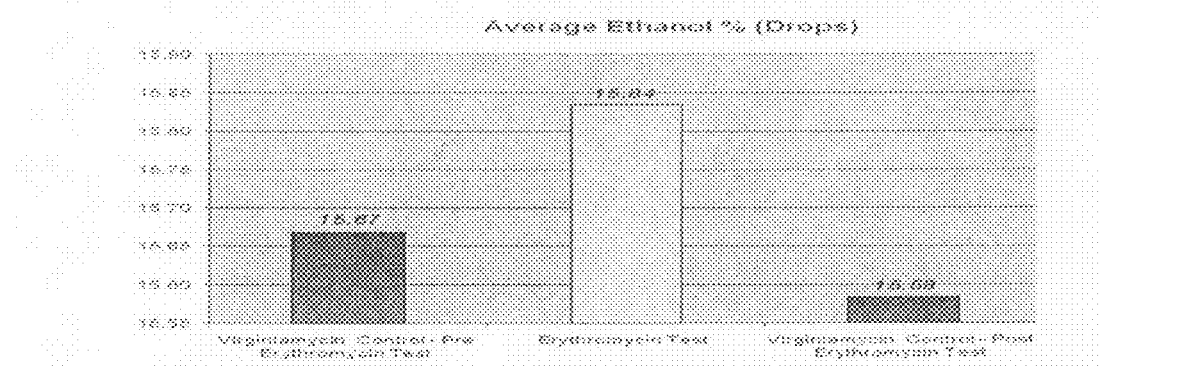
FIG. 2 is a graphical representation of the data from table 3.
Figure 3:
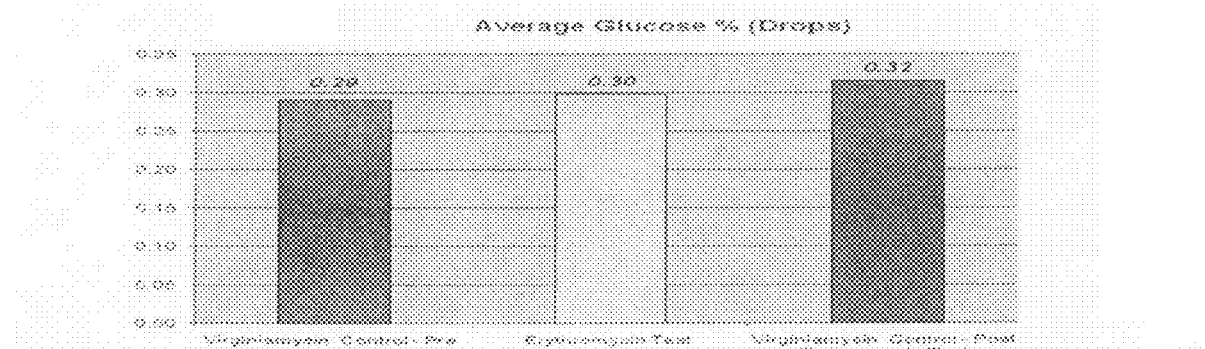
FIG. 3 is a graphical representation of the data from table 4.

The data presented in the graphs shown in FIGS. 1 through 3 indicates that prior to the use of Erythromycin in fermentation, contaminating bacteria were utilizing a greater percentage of the available carbohydrate to produce lactic acid and less carbohydrate was available for the yeast fermentation. During the Erythromycin trial, more carbohydrate was utilized by yeast for ethanol production. The "post trial" fermentors reflected a trend back towards lactic acid production by contaminating bacteria. Furthermore, during the erythromycin trial, lactic acid production decreased by 0.23 percent while ethanol production increased by 0.17 percent representing a production increase of 816 gallons of ethanol per fermentor.

Determination of Residual Levels of Bactenix V200 in Distillers Co-Products

This experiment determined if any residual levels of the Erythromycin were found in distillers co-products derived from fermentation batches in Set 2 above, in which Erythromycin was used as an antimicrobial agent. These trials were conducted in a 50 m/g/y fuel ethanol producing facility utilizing corn as a substrate. This facility is a dry grind, batch fermentation process producing both dried distiller's grains and solubles (DDGS) and wet distiller's grains and solubles (WDGS) utilizing 0.5 ppm Erythromycin. Six samples consisted of five DDGS and one WDGS were taken from co-products produced by fermentation batches solely utilizing Erythromycin.

All samples were refrigerated or maintained on ice packs preserving freshness and then shipped to Midwest Laboratories in Omaha, Neb. USA. Midwest Labs utilized liquid chromatogram quadrupole mass spectrometry (LC/MS) to test the samples with a low detection limit of 50 parts per billion. No Erythromycin was detected in any of the samples, indicating no Erythromycin was carried through to distiller's co-products. See results in Table 5.

TABLE 5

Distiller's co-product showing absence of Erythromycin

| Sample ID | Samples obtained from fermentation batches | Amount used in fermentation | Antimicrobial residual (limit 50 ppb) |
|---|---|---|---|
| DDGS 32307 | 5988 to 6015 | 0.5 ppm | Not Detected |
| DDGS 32607 | 5988 to 6015 | 0.5 ppm | Not Detected |
| DDGS 32707 | 5988 to 6015 | 0.5 ppm | Not Detected |
| DDGS 32907 | 5988 to 6015 | 0.5 ppm | Not Detected |
| DDGS 41607 | 5988 to 6015 | 0.5 ppm | Not Detected |
| WDGS 41607 | 5988 to 6015 | 0.5 ppm | Not Detected |

Impact of Erythromycin on the Function and Replication of *Saccharomyces cerevisea* During Alcohol Fermentation A study was conducted to determine if the fermentation antimicrobial Erythromycin, interfered with cell growth and the fermentation function of *Saccharomyces cerevisea* yeast used in the fermentation phase of the production of fuel ethanol. This study provided analysis of what impact, if any, the Erythromycin has on the yeast during lab scale fermentations, specifically BioFerm XR yeast from North American Bioproducts Corporation (NABC). This study looked at the ability of yeast to replicate and ferment a corn mash substrate with and without the presence of Erythromycin.

Procedure:

This study was set up in a series of fermentation vessels. All antibiotic concentrations were tested in triplicate. Cell counts were done on one flask for each treatment at 24 and 48 hours and final testing of the fermentation reactions by HPLC was performed at 48 hours. The experiment was set as follows:

1. Antibiotic solutions were prepared to provide a sterile 1 and 10 μg/ml solutions.
2. Antibiotic solutions tested were as follows:
   A. Control (NA), no antibiotic
   B. Erythromycin (5 ppm)
   C. Erythromycin (10 ppm)
   D. Erythromycin (20 ppm)
3. Fermentations were set up using 31% solids corn mash using saccharifying enzymes and the following procedure:
   A. Yeast Conditioning:
      1. Add 2 g yeast to 10 mil sterile water for each 3 flasks to test, (10 g yeast to 50 ml water) into a sterile 250 ml flask and place in water bath set to 100° F.
      2. Incubate at 100° F. for 30 minutes with occasional mixing.
      3. Remove flasks from water bath and divide suspension between the all flasks for the trial.
   B. Fermentation Procedure
      1. To prepared mash, add the following.
         a. Add 0.58 g urea/liter mash and mix.
         b. Add 0.2 ml GA per liter and mix.
      2. Remove sample for background HPLC testing.
      3. Add antibiotic solution to labeled sterile 250 ml flasks.
      4. Add hydrated yeast suspension to mash and mix well.
      5. Add sterile stir bar to each flask and add about 150 ml mash into each 250 ml flask for a total of 12 flasks. Three flasks for each trial as follows:
         a. First group, no antibiotic (NA) flasks 1-3
         b. Second group, Erythromycin (5 ppm), flasks 4-6
         c. Third group, Erythromycin (10 ppm), flasks 7-9
         d. Fourth group, Erythromycin (20 ppm), flasks 10-12
      6. Cover each flask with a gas trap in a sterilized stopper.
      7. Place in a 33° C. water bath with continuous mixing at 280 rpm at 75% power.
         a. Turn power on to the magnetic stirrers after placing the flasks onto the platforms to move the stir bars; make sure that mixing is occurring in the flasks.
      8. Remove sample at 24 hours and perform cell count.
      9. Incubate sample for 48 hours, enough time for complete fermentation
      10. Collect samples at the following times for HPLC testing:
         0 hours (one per treatment); 24 hours; 48 hours
         Perform 48 hour cell count on same flask as for 24 hour count.

As displayed in Table 6, there was no discernable adverse effect of Erythromycin on the yeast when used up to 20 ppm, which is four times the product's preferred dosage rate. The cell count data indicated that while there was some variation in cell counts, the viability and budding levels were comparable for the 4 sample sets.

The expected population dynamics in the samples between 24 to 48 hours was also very similar. There was a slight increase in cell counts for the 10 and 20 ppm Erythromycin samples at 48 hr, but this was most likely a sampling and recording artifact and not an actual increase for those samples, especially as the viability percent and budding percent for all sample sets are very similar. Based on the data from table 6 it can be deduced that at 48 hr the yeast growth is marginal better when the environment has Erythromycin present. Hence the yeast in an erythromycin environment tends to stay healthy and multiplies to produce higher amounts of alcohol.

All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept, spirit and scope of the invention. More specifically, it will be apparent that certain agents which are both chemically and physiologically related may be substituted for the agents described herein while the same or similar results are achieved. All such similar substitutes and modifications apparent to those skilled in the art are deemed to be within the spirit, scope and concept of the invention as defined by the appended claims.

The invention claimed is:

1. A method for increasing the amount of ethanol produced during large scale ethanol production comprising:
   introducing a fermentation mixture comprising yeast S. cerevisiae into a vessel used during ethanol production;
   introducing an antibiotic as an active agent to the vessel used during ethanol production, and fermenting the fermentation mixture by said yeast to produce ethanol;
   wherein the fermentation temperature is maintained between 30 to 38° C. and the fermentation pH is maintained between 2.5 to 6, and wherein the antibiotic is selected from the group consisting of Erythromycin and salts of Erythromycin, and
   said antibiotic is added to said vessel in an amount ranging from at least 0.5 ppm to about 6 ppm of the fermentation mixture, the antibiotic controls growth of lactic acid bacterial species present in the vessel during ethanol production without inhibiting the growth of said yeast in the vessel thereby resulting in increased ethanol production from the fermentation mixture.

2. The method of claim 1, wherein the antibiotic is added in an amount ranging from 0.5 to 3 ppm of the fermentation mixture.

TABLE 6

Impact of Erythromycin showing no hindrance in the growth of yeast cells

| | Time | Cell Count | % Viable | % Budding | Time | Cell Count | % Viable | % Budding |
|---|---|---|---|---|---|---|---|---|
| NA 0 ppm | 24 hr | 454 | 85 | 7 | 48 hr | 432 | 58 | 3 |
| Erythromycin 5 ppm | 24 hr | 467 | 82 | 8 | 48 hr | 430 | 63 | 5 |
| Erythromycin 10 ppm | 24 hr | 434 | 80 | 8 | 48 hr | 454 | 61 | 5 |
| Erythromycin 20 ppm | 24 hr | 431 | 85 | 7 | 48 hr | 446 | 62 | 4 |

Note:
1) Cell count is presented as the number of cells in a given area.
2) % viable is presented as the percent of cells that are thriving in a given area.
3) % budding is presented as the percent of daughter cells developed from the mother cells.

3. The method of claim 1, wherein the ethanol produced is fuel ethanol.

4. The method of claim 1, wherein the vessel is a fermentation tank and the antibiotic is introduced therein.

5. The method of claim 1, wherein the vessel is a yeast propagation tank and the antibiotic is introduced therein.

6. The method of claim 1, wherein the fermentation mixture is derived from a feedstock selected from the group consisting of: corn, wheat, triticale, barley, cassava, rye, graded starch stream rendered from said feedstocks, sugar cane, sugar beet, molasses, rice straw, potato waste, wood waste, switch grass, pine, municipal waste, food waste, alcoholic and non-alcoholic beverage industry waste and mixtures thereof.

\* \* \* \* \*